United States Patent [19]

Aguilar

[11] 4,344,931

[45] Aug. 17, 1982

[54] DRY DENTIFRICE POWDERS

[76] Inventor: Abel Aguilar, Los Capulies No. 270, Lima, Perú, 18

[21] Appl. No.: 253,386

[22] Filed: Apr. 13, 1981

[30] Foreign Application Priority Data

Dec. 18, 1980 [PE] Perú ......................................... 40856

[51] Int. Cl.$^3$ ........................... A61K 7/16; A61K 7/18
[52] U.S. Cl. ......................................... 424/52; 424/49
[58] Field of Search ..................................... 424/49–58

[56] References Cited

FOREIGN PATENT DOCUMENTS

| | | | |
|---|---|---|---|
| 284579 | 6/1966 | Australia ............................... | 424/49 |
| 544811 | 9/1922 | France .................................. | 424/49 |
| 892427 | 4/1944 | France .................................. | 424/49 |
| 131225 | 6/1978 | German Democratic Rep. ... | 424/49 |

*Primary Examiner*—Shep K. Rose
*Attorney, Agent, or Firm*—Holman & Stern

[57] ABSTRACT

A novel dry dentifrice powder composition, instantly transformable, into a smooth and homogeneous dental cream, when mixed with water, so that the user can prepare, instantaneously, his own dental cream. This is attained by incorporating an effective amount of one gum or mixture of several gums, to the conventional ingredients used in the dental powders.

16 Claims, No Drawings

DRY DENTIFRICE POWDERS

This invention relates to dry dentifrice powders, and more specifically relates to a dry dentifrice powder composition, comprising an effective amount of one gum or mixture of several gums, which, when mixed with a predetermined amount of water, converts, instantly into a smooth tooth paste or dental cream.

BACKGROUND OF THE INVENTION

Dentifrice powders are well known in prior art as composites comprising polishing agents, pH buffers, detergents and additional ingredients such as sweeteners, flavourings, colourings, antibacterial agents and fluorine-providing materials. Notwithstanding, due to the several inconveniences in the use of the dry dentifrice powders, such as the difficulties for dispensing it in the proper and required amount on the tooth brush and, principally, due to the unpleasant feeling and discomfort when the powders are applied in the oral cavity, said conventional dentifrice powders have a restricted use because consumers prefer the dental creams in spite of the lower cost of dental powders.

Conventional dental creams are also well known in the prior art as composites comprising dry ingredients and liquid ingredients. Generally the dental creams have a wider acceptance due to their creamy consistency and texture, easy application and better hygienic manipulation when used. The principal inconvenience of the conventional dental creams is that the liquid ingredients such as water, glycerin, sorbitol, etc., are presented in high percentage in the formulations which is necessary to form a creamy mass of desired consistency. Therefore, the conventional dental creams require large containers, usually expensive collapsible aluminium or lead tubes which unnecessarily increase the cost of the end product.

SUMMARY OF THE INVENTION

The present invention solves the aforementioned problems in the prior art by providing a dry dentifrice powder which is convertible instantaneously into a smooth cream of similar consistency, texture, general appearance and quality as the conventional dental creams when water is added by the user.

The invention consists in incorporating with those ingredients commonly used in conventional dentifrice powders, an effective amount of a gum or mixture of several gums in dry powder state, so as to form colloidal suspensions and/or solutions of desired viscosity, when sufficient amount of water is added by the user, thus transforming the powder instantaneously into a homogeneous dental cream or tooth paste.

It is necessary to point out that, at present, the term gum applies to water-soluble, thickening and gelling agents. The technical definition of a gum is a polymeric material that can be dissolved or dispersed in water to give a thickening and/or gelling effect. Since these materials are of colloidal nature, they are also referred to as hydrophilic colloids or hydrocolloids.

According to the present invention the gums can be used pure or coated with wetting agents to speed up their solubility in cold water.

The invention comprises also the dry dentifrice composition apt to be transformed, instantly, into a smooth dental cream or tooth paste, as desired.

According to these facts, the dry dentifrice powder, containing the active ingredients, the additional ingredients and the gum or mixture of several gums, all of them in dry powder state, can be easily and thoroughly mixed and packaged into low-cost suitable pouches or containers so that the user can prepare, instantly, his own dental cream.

OBJECTS OF THE INVENTION

An object of this invention is to provide a dry dentifrice powder that can be transformed, at the moment it is used, into a smooth dental cream.

Another object of this invention is to avoid the use of expensive collapsible aluminium or lead tubes, that are distinctive of the dental cream containers.

Other objects of the present invention are: to obtain a low-cost dentifrice by eliminating unnecessary liquid ingredients, simplification of its manufacturing process, elimination of the expensive conventional containers of the dental creams and, outstandingly reducing the transportation and storage costs.

These and other advantages of the invention will become apparent from the following description relating to one embodiment of the invention, given by way of example only, since certain changes can be made in carrying out the above process and products without departing from the scope of the invention or limiting the ambit of the appended claims.

DESCRIPTION OF THE PREFERRED EMBODIMENTS

The dentifrice powder of the invention is a dry and homogeneous mixture of the active and additional ingredients of the conventional dentifrice powders, plus the gum or mixture of several gums incorporated, ground to a fine mesh and thoroughly mixed in a standard rotary mixer.

The polishing ingredient may be any of the various products used in a conventional dentifrice, which do not harm the teeth. This ingredient may be a silica compound of a very fine particle size and/or calcium or magnesium salts of inorganic acids or their hydroxides or mixtures of said ingredients. This polishing agent may be employed in amount of 70 to 90 weight %, but preferably about 75-85 weight % in the tooth powder formulation. The particle of the polishing material employed has an average size of less than 40 microns, but preferably about 2 to 12 microns.

The surface active or detersive materials preferred in the composition of the present invention are such as to provide foaming and cleansing properties. These detergents are water-soluble organic compounds and may be anionic or cationic in nature. It is necessary to use water-soluble salts of higher fatty acid monoglycerides, higher alkyl sulphates (e.g. Sodium Lauryl Sulphate) and the like, generally from about 1.0 weight % to 5.0 weight %, but preferably from about 2.0 weight % to 4.0 weight %.

As pH regulating agents, or buffers alkaline citrates or tartrates may be used, due to their good buffering action.

In accordance with this invention, the principal ingredients of the dry dentifrice powder subject of this patent application, are those that can give a high and suitable viscosity and creamy consistency to the mass, when water is added to said dentifrice powder, as to convert it, instantly, into a dentifrice cream or tooth paste. These compounds are one or more selected from the group consisting of:

A. NATURAL GUMS: Arabic Gum, Tragacanth Gum, Karaya Gum, Larch Gum, Ghatti Gum, Locust Bean Gum, Psyllium Seed Gum, Quince Seed Gum, Agar, Algin, Alginates, Carrageenan, Carrageenates, Furcellaran, Pectin, Gelatin, Starches, and the like.

B. MODIFIED GUMS (SEMI-SYNTHETIC): Carboxymethycellulose, Methylcellulose, Hydroxypropylcellulose, Ethylhydroxyethylcellulose, Microcrystalline Cellulose, Carboxymethylstarch, Hydroxyethylstarch, Hydroxypropylstarch, Dextrans, Xanthan Gum, Propylene Glycol Alginate, Triethanolamine Alginate, Carboxymethyl Locust Bean Gum, Carboxymethyl Guar Gum, and the like.

C. COMPLETELY SYNTHETIC GUMS: Polyvinylpyrrolidone, Polyvinyl Alcohol, Carboxyvinyl Polymer, Polyacrylic Acid, Polyacrylamide, Ethylene Oxide Polymers, and the like.

The gum or mixture of gums are incorporated into the formulation from about 0.5 weight % to 20 weight %, but preferably from about 2 weight % to about 10 weight % so as to provide a creamy consistency when the dry dentifrice powder is mixed with water.

Other materials can be incorporated into the dentifrice powder formulations as flavourings, colourings, whitening agents, preservatives, antibacterial agents, fluorine-providing ingredients, etc.

Dry dentifrice powders as herein described are prepared and packaged into small, hermetically sealed, pouches or containers that can be easily warehoused, transported, sold and carried. The user has only to add a required amount of water to form, instantly, a paste or cream. This represents a practical and economical method for manufacturing and using dentifrice products.

EXAMPLE

Magnesium silicate: 86.5%
Arabic Gum: 3.8
Sodium Lauryl Sulphate: 2.4
Trisodium citrate: 3.0
Menthol: 2.0
Sodium saccharin: 0.1
Spray dried Cinnamon flavour: 2.2

I claim:

1. A method of instantly converting a dry powder dentifrice composition into a homogeneous dental cream comprising:
   (a) combining with components common to conventional dry dentifrice compositions, from 2% to 10% by weight, based on the weight of the dry powder dentifrice composition, of at least one readily water-soluble dry powdered gum and an amount of a magnesium or calcium silicate effective as a polishing agent, and
   (b) adding an amount of water sufficient to immediately convert the dry powder dentifrice composition into a homogeneous dental cream.

2. The method of claim 1, wherein said at least one readily water-soluble gum is selected from the group consisting of arabic gum, tragacanth gum, karaya gum, larch gum, ghatty gum, naturally occurring locust bean gum, psyllium seed gum, quince seed gum, agar, carrageenan, carrageenates, furcellaran, pectin, gelatin, starches, methylcellulose, hydroxypropylcellulose, ethylhydroxyethylcellulose, carboxymethylstarch, hydroxymethylstarch, hydroxpropylstarch, dextrans, xanthan gum, propyleneglycol alginate, triethanolamine alginate, carboxymethyl locust bean gum, carboxymethyl guar gum, polyvinylpyrrolidone, polyvinyl alcohol, carboxyvinyl polymers, polyacrylic acid, polyacrylamide, and ethylene oxide polymers.

3. The method of claim 1, wherein said at least one readily water-soluble gum is selected from the group consisting of arabic gum, larch gum and xanthan gum.

4. The method of claim 1, wherein said polishing agent is magnesium silicate.

5. The method of claim 1, wherein said effective amount of said polishing agent is 70% to 90% by weight, based on the weight of the dry powder dentifrice composition.

6. The method of claim 1, wherein said effective amount of said polishing agent is 75% to 85% by weight, based on the weight of the dry powder dentifrice composition.

7. The method of claim 1, wherein said common components comprise at least one of a detergent compound, a buffer, a coloring agent, a flavoring agent, a whitening compound, a preservative, an antibacterial agent and a fluorine-containing compound.

8. The method of claim 1, wherein the amount of water added is approximately 20% to 90% by weight, based on the weight of the dry powder dentifrice composition.

9. The method of claim 1, wherein the amount of water added is approximately 40% to 50% by weight, based on the weight of the dry powder dentifrice composition.

10. A dry powder dentifrice composition capable of being instantly converted into a homogeneous dental cream comprising:
    (a) between 2 to 10% by weight, based on the weight of the dry powder dentifrice composition, of at least one readily water-soluble dry powdered gum,
    (b) an amount of magnesium or calcium silicate effective as a polishing agent, and
    (c) other components common to conventional dry dentifrice compositions.

11. The dry powder dentifrice composition of claim 10, wherein said at least one readily water-soluble gum is selected from the group consisting of arabic gum, tragacanth gum, karaya gum, larch gum, ghatty gum, naturally occurring locust bean gum, psyllium seed gum, quince seed gum, agar, carrageenan, carrageenates, furcellaran, pectin, gelatin, starches, methylcellulose, hydroxypropylcellulose, ethylhydroxyethylcellulose, carboxymethylstarch, hydroxymethylstarch, hydroxypropylstarch, dextrans, xanthan gum, propyleneglycol alginate, triethanolamine alginate, carboxymethyl locust bean gum, carboxymethyl guar gum, polyvinylpyrrolidone, polyvinyl alcohol, carboxyvinyl polymers, polyacrylic acid, polyacylamide, and ethylene oxide polymers.

12. The dry powder dentifrice composition of claim 10, wherein said at least one readily water-soluble gum is selected from the group consisting of arabic gum, larch gum and xanthan gum.

13. The dry powder dentifrice composition of claim 10, wherein said polishing agent is magnesium silicate.

14. The dry powder dentifrice composition of claim 10, wherein said at least effective amount of said polishing agent is 70% to 90% by weight, based on the weight of the dry powder dentifrice composition.

15. The dry powder dentifrice composition of claim 10, wherein said at least effective amount of said polishing agent is 75% to 85% by weight, based on the weight of the dry powder dentifrice composition.

16. The dry powder dentifrice composition of claim 10, wherein said at least other components comprise at least one of a detergent compound, a buffer, a coloring agent, a flavoring agent, a whitening compound, a preservative, an antibacterial agent and a fluorine-containing compound.

* * * * *